US008700134B2

(12) United States Patent
Grego et al.

(10) Patent No.: US 8,700,134 B2
(45) Date of Patent: Apr. 15, 2014

(54) CANTILEVER-BASED MEMS OPTICAL SCANNING APPARATUS, SYSTEM AND METHOD

(75) Inventors: Sonia Grego, Durham, NC (US);
Kristin Hedgepath Gilchrist, Durham, NC (US); David Edward Dausch, Raleigh, NC (US); Michael Kasper Lamvik, Durham, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 46 days.

(21) Appl. No.: 13/259,791

(22) PCT Filed: Feb. 26, 2010

(86) PCT No.: PCT/US2010/025565
§ 371 (c)(1),
(2), (4) Date: Dec. 14, 2011

(87) PCT Pub. No.: WO2010/114654
PCT Pub. Date: Oct. 7, 2010

(65) Prior Publication Data
US 2012/0080612 A1 Apr. 5, 2012

Related U.S. Application Data

(60) Provisional application No. 61/166,410, filed on Apr. 3, 2009.

(51) Int. Cl.
*A61B 6/00* (2006.01)
(52) U.S. Cl.
USPC .......................... 600/478; 600/473; 600/476

(58) Field of Classification Search
USPC ................................................. 600/473–480
See application file for complete search history.

(56) References Cited

U.S. PATENT DOCUMENTS

| 5,774,220 | A | 6/1998 | Wienecke |
| 5,784,162 | A | 7/1998 | Cabib et al. |
| 6,127,681 | A * | 10/2000 | Sato et al. ........................ 850/26 |
| 6,211,666 | B1 | 4/2001 | Acker |
| 7,557,916 | B2 * | 7/2009 | Bakker et al. ................. 356/317 |
| 7,570,363 | B2 * | 8/2009 | Takahashi ..................... 356/479 |

(Continued)

OTHER PUBLICATIONS

International Search Report Issued Apr. 23, 2010 in PCT/US10/025565 filed Feb. 26, 2010.

(Continued)

*Primary Examiner* — Sanjay Cattungal
(74) *Attorney, Agent, or Firm* — Oblon, Spivak, McClelland, Maier & Neustadt, L.L.P.

(57) ABSTRACT

The present invention relates to an optical scanning apparatus and an optical scanning system The optical system includes an optical engine connected to an optical scanning probe The optical scanning probe images a sample at different lateral positions of the sample The optical scanning probe includes a housing having a longitudinal axis extending in a direction towards a sample to be scanned, a first base having a first moveable mirror supported thereon by a first cantilever connecting the first moveable mirror to the first base, a second base having a second moveable mirror supported thereon by a second cantilever connecting the second moveable mirror to the second base, and a support attaching the first and second bases so that the first moveable mirror and the second moveable mirror are disposed along the longitudinal axis apart from each other.

44 Claims, 10 Drawing Sheets

(56) References Cited

U.S. PATENT DOCUMENTS

| | | | |
|---|---|---|---|
| 7,573,627 B2* | 8/2009 | Mills et al. ................. 359/224.1 |
| 7,999,945 B2* | 8/2011 | Zara .............................. 356/479 |
| 2001/0055462 A1 | 12/2001 | Seibel |
| 2002/0008091 A1 | 1/2002 | Brandinger et al. |
| 2002/0064341 A1 | 5/2002 | Fauver et al. |
| 2002/0089254 A1 | 7/2002 | Dausch et al. |
| 2002/0135850 A1 | 9/2002 | Hagelin et al. |
| 2003/0081651 A1 | 5/2003 | Gianchandani et al. |
| 2004/0122289 A1 | 6/2004 | Mizuno |
| 2004/0240779 A1 | 12/2004 | Yeh et al. |
| 2006/0091334 A1* | 5/2006 | Urbach et al. ........... 250/559.45 |
| 2006/0196852 A1 | 9/2006 | Bann et al. |
| 2006/0261263 A1 | 11/2006 | Ishihara et al. |
| 2007/0158552 A1 | 7/2007 | Kim et al. |
| 2007/0238955 A1 | 10/2007 | Tearney et al. |
| 2008/0106777 A1 | 5/2008 | Weir |

OTHER PUBLICATIONS

Office Action issued Feb. 25, 2013, in European Patent Application No. 10 759 178.6.

Extended European Search Report issued Jul. 11, 2012 in European Patent Application No. 10759178.6.

* cited by examiner

FIG. 4D
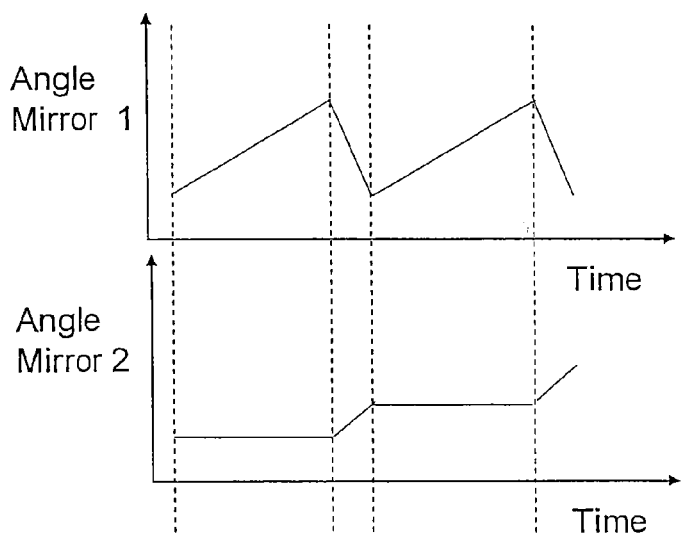
FIG. 4E(1)
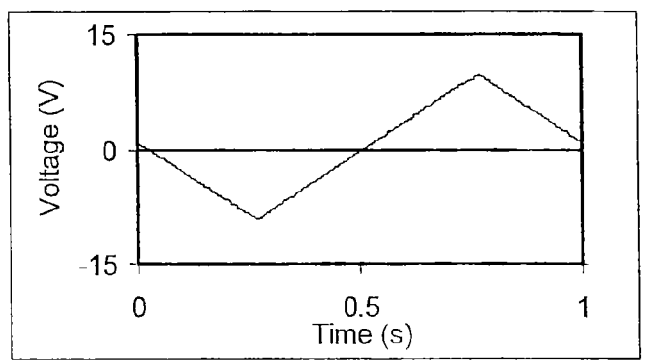
FIG. 4E(2)
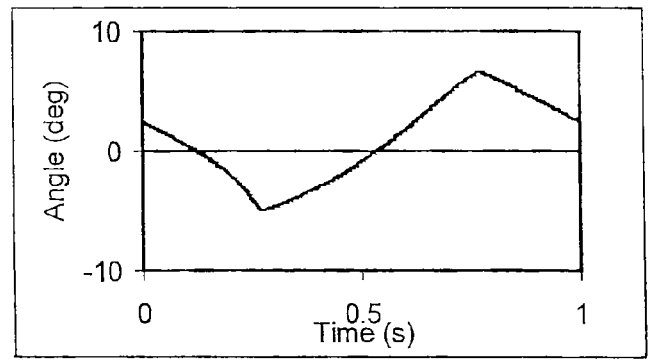

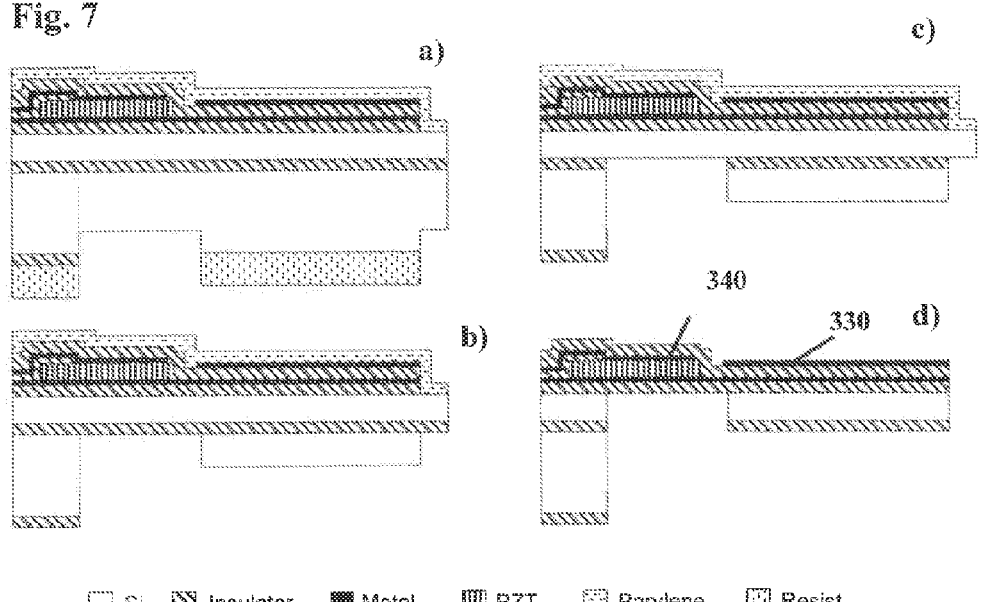

CANTILEVER-BASED MEMS OPTICAL SCANNING APPARATUS, SYSTEM AND METHOD

BACKGROUND OF THE INVENTION

1. Field of Invention

The present invention relates to MEMS-based optical scanner systems for endoscopic optical imaging of tissues and other biomedical specimens.

2. Discussion of the Background

The endoscopic system for the observation of the interior of a patient's body typically includes an elongated insertion tube ending with an optical window and connected to an external unit. The external unit is also known as the optical engine and contains the light source or sources, the detector and the processing unit. A light beam from the light source is delivered to and from the sample typically by an optical fiber. A variety of high resolution optical imaging modalities can be used to augment the conventional white light endoscopic observation including Optical Coherence Tomography (OCT), single and multi-photon fluorescence, confocal fluorescence, Raman etc. In the case of high resolution imaging, the light beam 2 needs to be focused and scanned on the sample 4 by a scanning mechanism 6 located at the distal end of the endoscope as shown in FIG. 1A.

Optical Coherence Tomography (OCT), an emerging optical technology analogous to ultrasound, is an interferometric technique providing microscopic tomographic sectioning of biological samples with mm-range penetration capability in tissue. By measuring singly backscattered light as a function of depth, OCT provides subsurface imaging with high spatial resolution (~10 µm) within a depth range of 1 to 4 mm in vivo with no need for fluorescent labeling of the tissue under investigation. OCT has been demonstrated to provide accurate sub-surface imaging of highly scattering tissues in the mucosa of gastrointestinal, respiratory, and urogenital tracts as well as in the oral cavity and in the endothelium of vascular tissue. The imaging capability of OCT permits accurate non-invasive diagnosis and staging of cancers and other pathologies that heretofore have been difficult to diagnose at an early stage because of the relatively poor visualization available with white light endoscopy and ultrasonic techniques.

OCT relies on interferometry using a low-coherence light source to achieve imaging depth having an axial resolution that is inversely proportional to the source bandwidth. Sources that have been used to implement OCT are, for example, superluminescent diodes, pulsed lasers and swept-wavelength lasers. A typical source center wavelength is 1310 nm and typical source bandwidth ranges from 70 nm to 100 nm. In the OCT apparatus shown in FIG. 1B, the source light 8 is coupled into an optical fiber 10 and then split, for example by a fiber coupler 16, so that the light beam goes both through a reference arm 20 and also through a probe arm 22 to the tissue sample 4 to be imaged. The light from the reference arm 20 is reflected from a reference mirror (not shown), and the light from probe arm 22 is reflected from the tissue sample 4. Both reflections are directed back through the fiber coupler 16, and detector 12 detects interference of the two reflected beams, according to a difference in path lengths. Detection of back reflected signal has been demonstrated using different approaches, such as time domain OCT and Fourier domain OCT. In time-domain OCT the reference mirror is physically moved such that the reference path length changes, so that light reflections from different depths of tissue are sampled. An alternate approach to time-domain OCT, called Fourier-Domain OCT (FDOCT), has been shown to have significant advantages in speed and signal-to-noise ratio. In the Fourier-Domain method, the reference mirror is fixed, and the Fourier Transform of the signal is performed based on either a spectrometer-based receiving unit with a line scan camera or a swept-wavelength laser source. A computer system performs the processing steps for the image acquisition, analysis and display.

For endoscopic applications of OCT, the focused illumination beam needs to be scanned across the sample in order to obtain a tomographic image which represents a line on the sample (for one dimensional scanning) or an area of the sample (for two dimensional scanning). Since the depth information is provided by the interferometer arm in OCT, a 2D beam scanning image provides a 3D volumetric image. Two probe designs have been used in endoscopic optical imaging: side-looking and forward-looking.

Side-looking endoscopes have been developed based on configurations of rotating or translating fiber and micro-optics for imaging into a side-looking geometry. Side-looking catheter OCT probes have included both rotational-scanning and linear-scanning, the former performing a circumferential scan around the probe perimeter and the latter performing a linear scan along one probe radius. A third dimension can be added by mechanically pulling the cable along the longitudinal axis; however, this procedure has limited accuracy.

One advantage of forward looking OCT probes is their ease of integration for operation with a forward-looking optical endoscope, so that an optical image is co-registered with a coherence tomography image, as both the optical image and the tomography image are obtained from the tip of the endoscope, which can be positioned by the operator against the surface of the internal organ to be investigated.

Side-looking probes have performed well in tightly restricted organs such as the esophagus. However, side-looking probes are less successful in probing the mucosa of larger or hollow organs such as the stomach, colon, and bladder. In particular, it is quite difficult to position side-looking probes to accurately image polyps in the colon, which is one potentially promising application of EOCT. Forward-looking probes are also advantageous over side-looking for applications of image-guided surgery and intravascular imaging to detect vascular defects such as vulnerable plaques.

The design of a forward-looking OCT imaging endoscope is complicated by the need to fit a two-dimensional optical beam steering system inside the endoscope. Forward-looking imaging has been achieved by scanning a single-mode optical fiber at the distal end of an endoscope with a variety of actuators; for example, piezoelectric ceramic or electroactive polymer actuators bonded to the fiber. The conventional scanning-fiber approach may exhibit drawbacks such as a requirement of a long rigid actuator component at the distal end of the probe (which limits flexibility) or the drawback of achieving large displacements at the expense of speed. The use of galvanometers or other macroscopic scanning mechanisms limits the ability to produce a forward-looking small diameter flexible probe.

SUMMARY OF THE INVENTION

The invention overcomes the problems and disadvantages of prior work as described in the various embodiments below.

In one embodiment of the invention, there is provided an optical scanning apparatus including a housing having a longitudinal axis extending in a direction towards a sample to be scanned, a first base having a first moveable mirror supported thereon by a first cantilever connecting the first moveable mirror to the first base, a second base having a second moveable mirror supported thereon by a second cantilever connecting the second moveable mirror to the second base, and a support attaching the first and second bases so that the first moveable mirror and the second moveable mirror are disposed along the longitudinal axis apart from each other. One of the first and second cantilevers angularly separated from the base at a position between a range of positive and negative angular motion for at least one of the first and second mirrors.

In one embodiment of the invention, there is provided an optical scanning system including an optical scanning probe configured to image a sample at different lateral positions of the sample. The optical scanning probe includes a housing having a longitudinal axis extending in a direction towards a sample to be scanned, a first base having a first moveable mirror supported thereon by a first cantilever connecting the first moveable mirror to the first base, a second base having a second moveable mirror supported thereon by a second cantilever connecting the second moveable mirror to the second base, and a support attaching the first and second bases so that the first moveable mirror and the second moveable mirror are disposed along the longitudinal axis apart from each other. One of the first and second cantilevers angularly separated from the base at a position between a range of positive and negative angular motion for at least one of the first and second mirrors. The optical system includes an optical engine connected to an optical scanning probe.

In one embodiment of the invention, there is provided a forward looking optical probe including a housing having a longitudinal axis extending in a direction towards a sample to be scanned, a first base including a first moveable mirror and a first cantilever, a second base including a second mirror, and a support attaching the first and second bases so that the first moveable mirror and the second mirror are disposed along the longitudinal axis apart from each other to provide forward imaging of the sample. The first cantilever is angularly separated from the base at a position between a range of positive and negative angular motion for the first mirror.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 4D is a schematic of a voltage raster control for the scanning probe of the present invention;

FIGS. 4E(1) and 4E(2) are schematics showing a triangular voltage waveforms applied to the cantilever arm of the scanning probe of the present invention and the resultant angular motion;

FIGS. 7A-7D are schematics of another MEMS fabrication process of the present invention;

DETAILED DESCRIPTION OF THE INVENTION

Figure 1A:
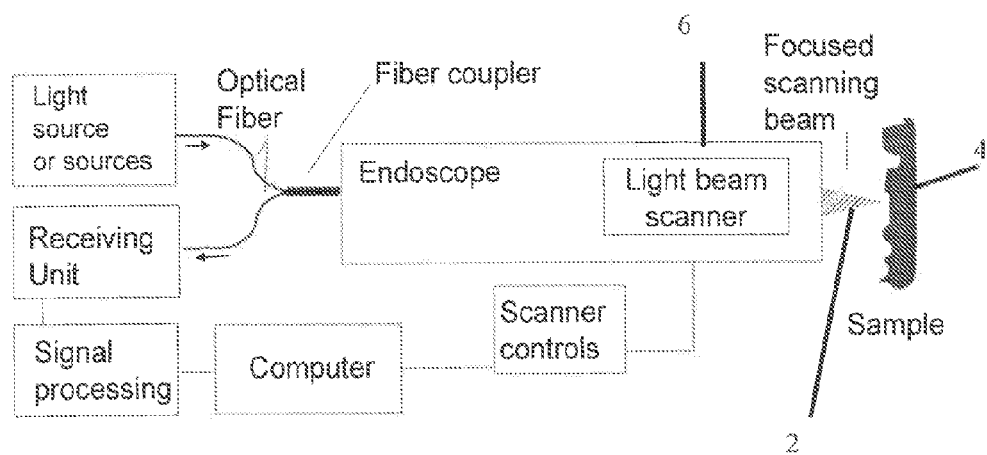
FIG. 1A is a schematic of a conventional endoscopic optical scanning system.
Figure 1B:
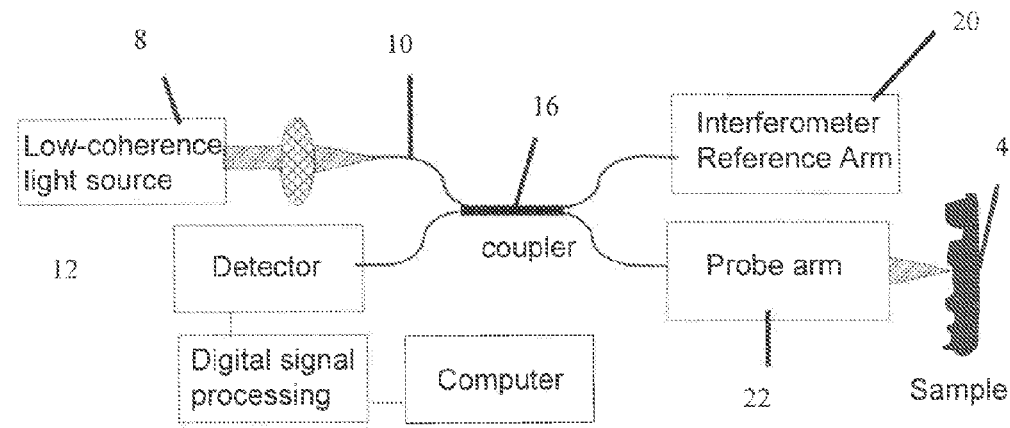
FIG. 1B is a schematic of an OCT system.
Figure 1C:
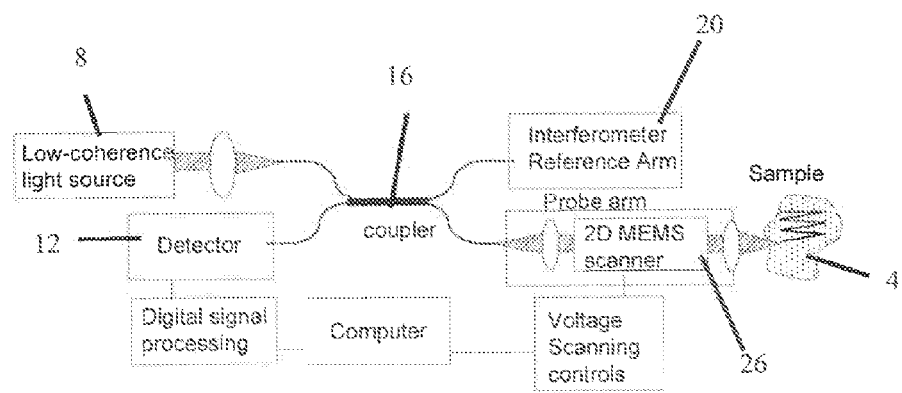
FIG. 1C is a schematic of an OCT system with the probe of the present invention

Referring now to the drawings, wherein like reference numerals designate identical, or corresponding parts throughout the several views, one preferred embodiment of the present invention, as represented in FIG. 1C, FIG. 1C is a schematic of an optical scanning system including a scanning unit of the present invention. The optical scanning system in FIG. 1C includes a low coherence light source 8, a fiber coupler 16, an interference reference arm 20, an endoscopic two-dimensional scanner 26, and a detector 12. The endoscopic two-dimensional scanner in one embodiment of the present invention is a MicroElectroMechanical Systems (MEMS) two-dimensional (2D) optical scanning mirror system. MEMS mirrors offer the advantages of large angle beam steering capability, rapid and selectable scanning speed, low power consumption and low-cost deriving from batch fabrication of the scanning devices. While side-looking MEMS-based scanning probes have been reported, the technology for making side-looking MEMS-based scanning probes cannot be used in a forward looking probe because of size constraints. Forward looking probes have been demonstrated previously using MEMS techniques for fabrication, but with actuation in only one direction because of space limitations.

In the MEMS two-dimensional (2D) optical scanning mirror system of the present invention, the scanning capability in one embodiment is based on piezoelectric cantilevers permitting in one aspect of the invention endoscopic forward-looking 3D Optical Coherence Tomography (OCT) to be realized with this probe. Light from the light source illuminates the sample according to respective positions of cantilevered mirrors (to be discussed in more detail later), and is collected from the sample and analyzed by the detector.

In more detail of this embodiment, a low-coherence light beam is directed to a reference arm 20 and to a forward-looking endoscopic probe 26. The light beam is directed to the tissue sample 4 via a forward looking endoscopic probe 26 which contains a 2D optical scanning device capable of scanning the surface of the tissue sample in both the x and y directions. The probe delivers a low-coherence light source to the surface of the tissue sample 4 and collects the light back scattered from the sample. Depth scanning of the tissue sample 4 may be accomplished by Fourier-Domain Optical Coherence Tomography (discussed above), and three dimensional images of the tissue sample can be obtained.

Figure 2:
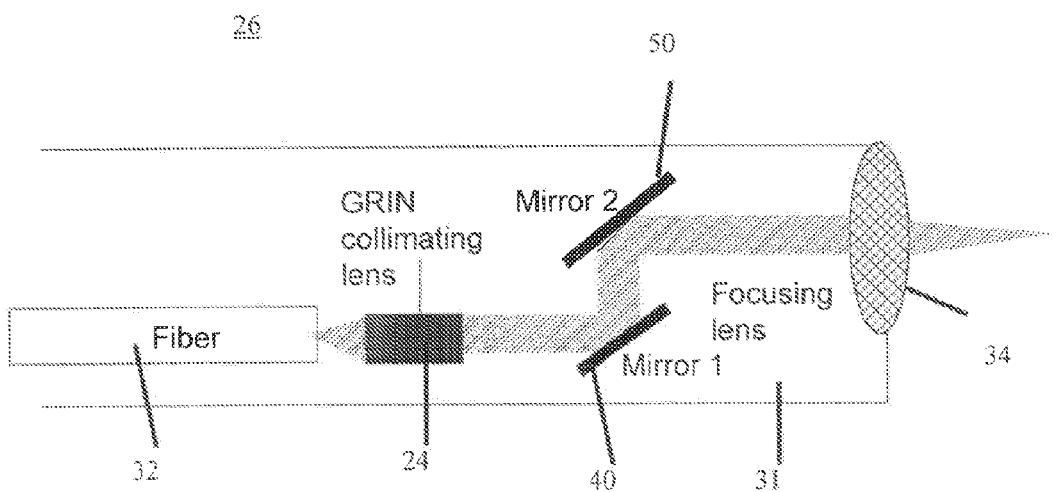
FIG. 2 is a schematic of a scanning unit of the present invention.

The endoscopic probe 26 of FIG. 1C, is further explained with reference to FIG. 2. FIG. 2 is a schematic of a scanning unit of the present invention. The endoscopic probe 26 is capable of performing two dimensional raster scanning by using two MEMS based mirrors 40 and 50 moving, in principle, orthogonal to one another to direct a light beam through a focusing lens 34. The probe includes a housing 31 containing inside the mirror apparatus and optical lenses. If the housing 31 is not a biocompatible tubing (i.e. a catheter) it can be inserted in a catheter. An optical fiber 32 inside the length of the probe 26 is used to deliver light from the source and collect light reflected from the tissue sample 4 back to a detector 12 for analysis.

In FIG. 2, at the distal end of the endoscopic probe, at the optical interface between the optical fiber 32 and the first mirror 40, is a fiber interface lens 24, such as for example a Graded-Index (GRIN) collimating lens. On the opposite end of the scanning unit is a focusing lens 34 providing an optical interface between the 2D scanner and the light transmitted to or received from the sample 4. Finally, the components of the endoscopic probe are contained in a housing 31, which in one embodiment is cylindrical to permit insertion of the probe into a standard catheter (used for medical applications).

Figure 3A:
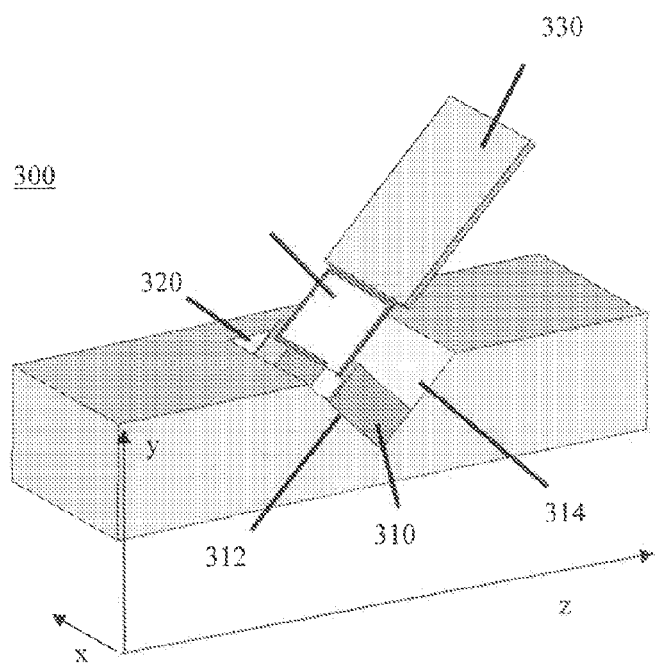
FIG. 3A is a schematic of a mirror block assembly of the present invention.

FIG. 3A is a schematic of a mirror block assembly of the present invention. FIG. 3A shows cantilevered mirror assembly 300 including a base block 350 with a lateral V-groove 310 extending part of the way across the width of base block 350. Other techniques which would provide placement and orientation of the cantilevered-mirror assembly on the base could be used in the present invention. FIG. 9 (to be discussed in more detail below) shows the probe according to one embodiment of the present invention in which mirror assemblies 300 and 400 are mounted in housing 250. As shown in FIG. 3A, V-groove 310 has two primary surfaces 312 and 314 which are shown at a 90 degree angle to each other and at a 45 degree angle to the top surface of the base block 350. Mirror assembly 300 further includes a handle 320, cantilevered mirror 330, and cantilever arm 340. Cantilever arm 340 is attached at one end to one side of the mirror 330 and at the opposite end to handle 320. Unless activated, cantilever arm 340 is designed to support mirror 330 in a neutral position approximately parallel to V-groove surface 314, at a 45 degree angle to the top surface of block 350. Other neutral positions could be designed for use in other embodiments. Accordingly, cantilever arm 340 has an angular deflection starting position removed respectively from the base (i.e., base block 350) and has an angular deflection range which deviates to either side of the starting position. In other words, the first cantilever arm 340 (and thus first mirror 330) is angularly separated from the first base 350 at a position between a range of positive and negative angular motion from the starting position for the first cantilever arm 340 (and thus first mirror 330).

The assembly and operation of the endoscopic probe will be described with reference to axes x, y and z of the base block 350. After assembly, the z axis of the base block will be aligned with the longitudinal axis of the cylindrical housing 31.

The mirror assembly 300 is positioned inside the housing 31 of the endoscopic probe 26 such that the base block 350 is oriented with the z axis and the bottom of the base block 350 is attached to an inside element (base mount 500 shown in FIG. 9a) of the housing 31. The mirror 330 is oriented to face the fiber end of the housing 31 but with the top of the mirror tilted back at a 45 degree angle away from the fiber end. When activated, cantilever arm 340 will bend, causing mirror 330 to move a few degrees in either direction in an arc in a y-z plane. Typical voltages range between −50 and +50 volts in some embodiments and in other embodiments voltages from −10V to +10V are used. The voltage is applied to metal contact pads fabricated according to standard microelectronic techniques, and contact is made through wire-bonding or any other method known to those skilled in the art. Electrical wiring is delivered to the device through the catheter and suitable openings (shown in FIG. 9b) in the base mount 500. The wires are bonded using glue or solder or other known methods to the base block 350 which contains metal traces. Metal traces in the base block 350 are electrically connected to the microfabricated cantilever mirrors through wirebonding or other known methods.

Figure 3B:
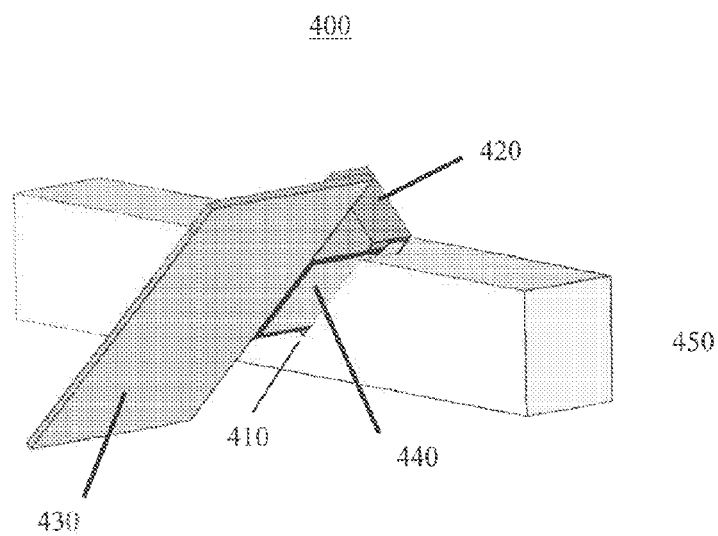
FIG. 3B is a schematic of another mirror block assembly of the present invention.

Mirror assembly 400 will now be described with reference to FIG. 3B. FIG. 3B is a schematic of another mirror block assembly of the present invention. Mirror assembly 400 has similar construction to assembly 300 with a base block 450, V-groove 410, handle 420, mirror 430 and cantilever arm 440. The position of mirror 430 at a neutral state is parallel to the plane of V-groove surface, but mirror 430 faces the opposite direction to groove surface.

Further, when cantilever arm 440 bends, the mirror moves through an arc which is perpendicular to V-groove surface. More importantly, this plane is also perpendicular and lateral to the face of mirror 330 when cantilever arm 340 is in a neutral state.

Figure 4A:
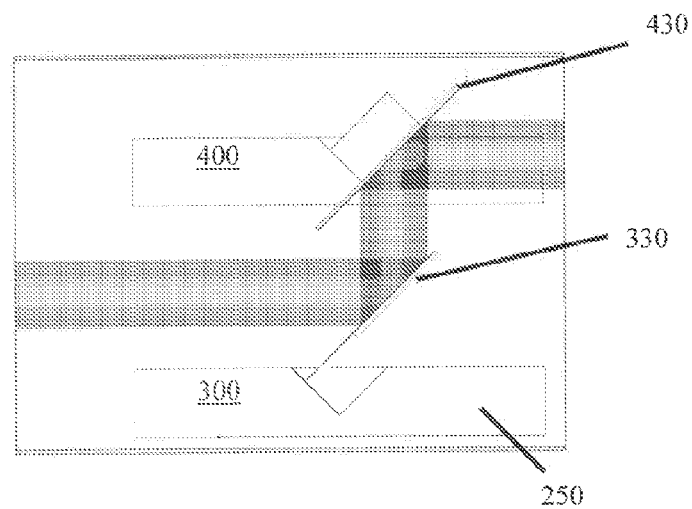
FIG. 4A is a schematic of a scanning probe apparatus of the present invention

As noted above, FIG. 4A shows the probe according to one embodiment of the present invention in which mirror assemblies 300 and 400 are mounted in housing 250. When assembly 400 is mounted opposite to assembly 300 in the housing 250, as shown in FIG. 4A, mirrors 330 and 430 are parallel and facing each other. When the mirrors are positioned in a neutral state, a light beam entering housing 250 in the z direction, from the fiber end to strike mirror 330, will reflect off mirror 330 in the y direction to mirror 430 and then reflect off mirror 430 in the z direction to the focusing lens 34, as shown in FIG. 4A.

Figures 4B, 4C:
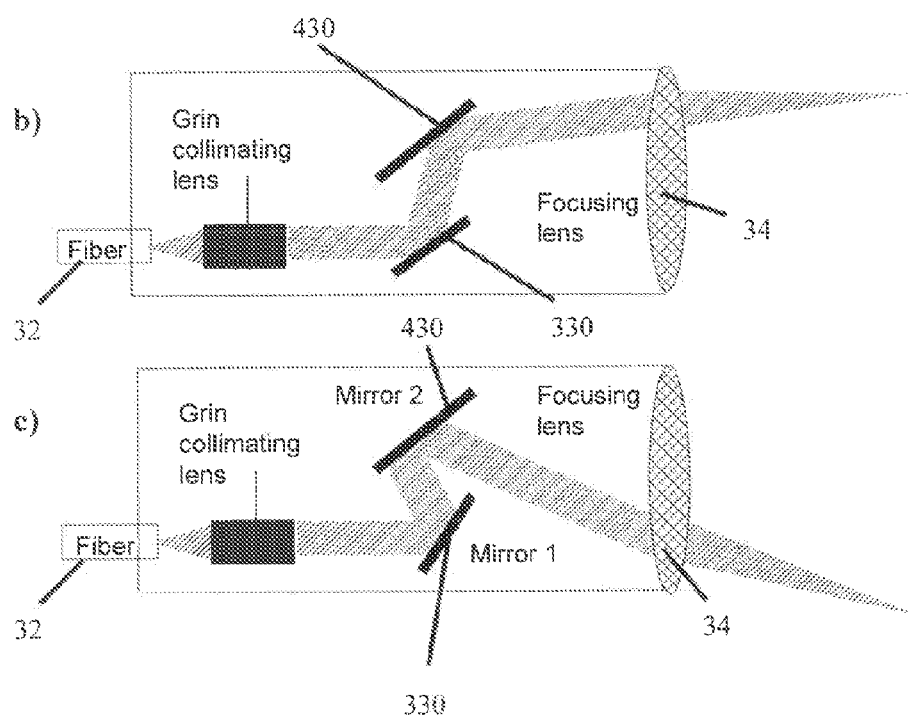
FIG. 4B is a schematic of mirror deflections inside the scanning probe of the present invention.
FIG. 4C is another schematic of mirror deflections inside the scanning probe of the present invention.

The operation of the mirror assemblies and method by which they are combined to provide a 2D raster scanning capability will now be explained with reference to FIGS. 4B and 4C. FIGS. 4B and 4C are schematics of mirror deflections inside the scanning probe of the present invention.

With both cantilevered mirrors 330 and 430 in their neutral state (FIG. 4A), a light beam enters from the fiber end lens along in the z direction to the center of the face of mirror 330. The light beam will be reflected from the center of mirror 330 to the center of mirror 430 and then be further reflected to the focusing lens 34. With mirror 430 in a neutral state, if cantilever arm 340 is activated to bend mirror 330 to a lower angle with respect to the surface of base block 350 (FIG. 4B), the incident light beam will strike at a higher point on the face of mirror 330, be reflected to a point higher on the face of mirror 430, and be further reflected to a position above the neutral position impinging point on the focusing lens 34.

If cantilever arm 340 is activated to bend mirror 330 to a higher angle with respect to the surface of base block 350 (FIG. 4C), the incident light beam will strike lower on mirror 330 and be reflected to a point lower on mirror 430 and further reflected to a position below the neutral position impinging point on the focusing lens 34. Thus, the angular deflection of mirror 330 corresponds to a movement of the light beam along the y axis of the focusing lens 34 and permits angular deviation to either side of the neutral starting position.

Regarding the action of mirror 440, if cantilever 340 is maintained in a neutral position while cantilever 440 (the upper cantilever) is bent either direction from its neutral state which sweeps an angle in the y-direction, light reflected from mirror 430 will be directed at an angle left or right of the center of focusing lens 34. When both cantilever arms are deflected from their respective neutral states the light beam can be directed simultaneously in both the x and y directions from center, to the maximum ranges of each mirror, thus defining the maximum surface area which can be scanned by the device. In one embodiment of the present invention, a rastering effect can be accomplished by manipulating one mirror to quickly oscillate about its neutral position (i.e. sweep the light beam back and forth) while slowly moving the angle of the other mirror (or incrementally stepping) it in a given direction. FIG. 4D is a schematic of a voltage raster control for the scanning probe of the present invention. The manipulation of the arms is performed with electrical signals where a higher voltage creates a sharper bend in the cantilever arm. FIG. 4D shows synchronized graphs of voltage over time as an example of how 2D rastering can be achieved. With regard to the voltage graphs, as the voltage for Mirror 1 is raised, the mirror angle increases and causes the beam to sweep in one dimension while the other mirror is held in a fixed position. Each time the voltage for Mirror 1 is reduced, allowing the mirror to sweep back the other direction, the voltage for Mirror 2 is increased slightly. In this way, each sweep of the beam in, for example, the x direction is incrementally shifted in the y direction from the previous sweep.

FIG. 4E(1) and 4E(2) are schematics showing a triangular voltage waveforms applied to the cantilever arm of the scanning probe of the present invention and the resultant angular motion. In particular, the exemplary triangular driving voltage ranges from −10V to +10 V to activate the cantilever mirror. A bias offset of 6V was added to the driving voltage. Under these drive conditions, the corresponding angular mirror deflection is shown in FIG. 4E(2) to be +/−5.5 degrees.

Because of the raster operation, the most compact mirror size accomplishing the task of intercepting the light beam at all times is rectangular, with the length (the dimension along the cantilever direction) and the width determined by its angular displacement and, in one aspect of the invention, sized to intercept the beam when fully tilted upward and downward. Mirror 1 is at least as wide as the light beam width, and it is longer than wider (aspect ratio length/width larger than 1), with a length determined by its angular displacement and one aspect of the invention to intercept the beam when fully tilted upward and downward. Mirror 2's length is also determined by its angular displacement and, in one aspect of the invention, sized to intercept the beam width when fully tilted upward and downward; mirror 2's width is typically larger than its length (aspect ratio length/width less than 1) because of one aspect of the invention to intercept the beam deflected by mirror 1. Square mirrors with the largest of the two dimensions would also accomplish the task, at the expense of a larger size of the apparatus. Example of mirror size which would allow scanning of a 500 μm beam diameter within a 3 mm catheter are mirror 1: 840 μm long×600 μm wide (area: 0.5 mm$^2$) and mirror 2: 840 μm long and 1600 μm wide (area 1.35 mm$^2$). Thus, the configuration with rectangular mirrors can maximize scan range and can minimize the apparatus size.

The above description of rastering in two dimensions to deliver a light source to a tissue sample also applies to the collection of light reflected from a tissue sample. Typically in optical endoscopic technology, source light is delivered and reflected light is collected simultaneously by the same minors; light is both delivered and collected from different regions with the movement of the mirrors. Alternatively, if the retroreflecting geometry is not used, the probe of the present invention can be used for other purposes such as collecting light from a sample that is illuminated by a secondary source; or to illuminate in a raster pattern a region whose reflection/scattering/fluorescence is detected by another probe or to illuminate in a raster pattern a region using a light beam having the function of ablation, thermal heating or other photo-therapy of the tissue.

One impediment for medical application, which the probe of the present invention addresses in its scanning unit design, is the difficulty of creating an endoscopic probe that is small enough to fit into a standard catheter insert. Another impediment for medical application, which the probe of the present invention addresses in its scanning unit design, is the difficulty of having enough mirror deflection control to provide sufficient angular deflection of the mirrors to capture a sizeable tissue image and also to have a high enough oscillation frequency to achieve fast image acquisition. Low-power operation and low manufacturing cost are important design considerations which the present invention also addresses in its scanning unit design.

In one embodiment of the present invention, actuation of mirrors of mm-size or less is facilitated by using MEMS technology to produce actuatable piezoelectric cantilever-based mirrors.

Piezoelectric MEMS actuators, when compared to other technologies such as thermal bimorph or electrostatic comb drive, have comparable maximum force, but are superior in resonance frequency and displacement resolution. Piezoelectric MEMS actuators exhibit larger static displacement and lower voltage actuation than electrostatic MEMS; for example electrostatic MEMs achieve static mechanical angle deviation of ±0.5° for 50 V and achieve a few degrees mechanical angle deviation only if operated at the resonance frequency, which causes non-uniform rastering speed and requires optical image correction. Electrostatic MEMS also exhibit issues of charge accumulation which degrades performance over time and causes stiction; they also typically have a small ratio of mirror size/device size.

Thermoelectric actuators require heating of the cantilever to hundreds of degrees Celsius and exhibit heat dissipation issues, among which is a limitation in the response time (maximum operating frequencies ranges from 100 to 500 Hz). Thermoelectric actuators are driven with relatively large current (tenths of milliamperes), which requires large diameter electrical wires. Magnetically driven MEMS require the addition of bulky electromagnets placed near the mirror devices; magnetically driven MEMS are also limited to operation at frequencies lower than 500 Hz. Piezoelectric MEMS do not require heating or additional actuating mechanisms; piezoelectric MEMS are driven at low voltages and low currents (e.g. microamperes); piezoelectric MEMS can operate at frequencies larger than 1 kHz, and can achieve large angular displacements in static conditions. Piezoelectric MEMS actuators are therefore especially suited for compact optical systems. Moreover, piezoelectric devices can detect their deflection by measuring the piezoelectrically generated current as function of strain thereby permitting feedback without the need of additional sensors.

In the previous descriptions of assemblies 300 and 400, the mirrors 330 and 430 were described as being attached to cantilever arms 340 and 440 but in one embodiment these assemblies are fabricated together as composite units with the feature of a thin piezoelectric arm on one end and a thick, flat, mirror surface on the other end. The steps of the fabrication process will be described with reference to FIGS. 5A-5F and 6A-6D. These steps are provided for illustration purposes and are not provided to limit the present invention to the specific details provided below. FIGS. 5A-5F are schematics of a MEMS fabrication process of the present invention.

Mirror and cantilever arm units were fabricated on 100 mm silicon wafers with 250-500 nm of thermal silicon dioxide. Before completing the front side process sequence, an additional silicon dioxide layer (2-3 μm) was deposited on the back sides of the wafers by plasma enhanced chemical vapor deposition (PECVD) to serve as a later etch mask.

Figure 5:
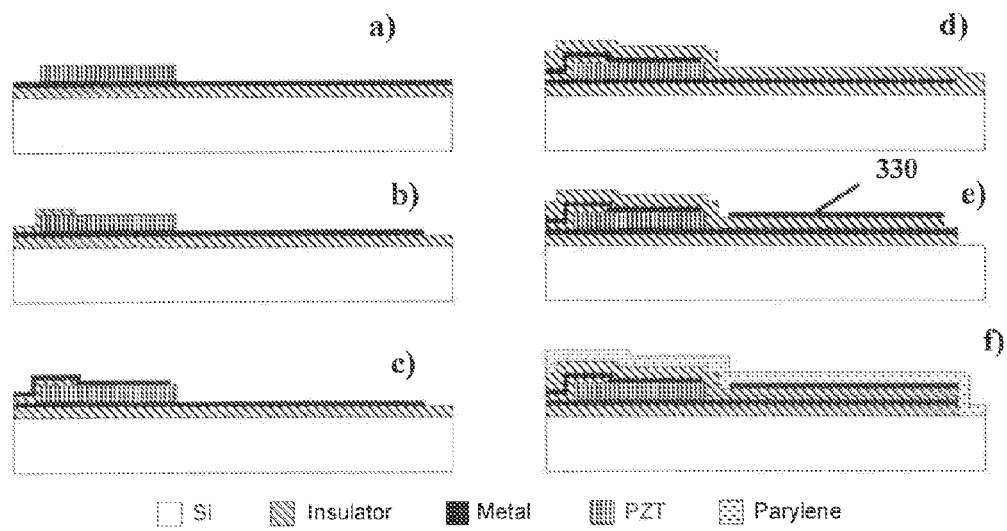
FIGS. 5A-5F are schematics of a MEMS fabrication process of the present invention.

The front side process sequence was used to fabricate the piezoelectric actuator and a reflective mirror. As shown in FIG. 5A, the bottom electrode was deposited by electron beam evaporation of Ti (25 nm) and Pt (150 nm). For the piezoelectric layer, $Pb(Zr0.53Ti0.47)O3$ (PZT) was spin-coated from metal organic precursors and annealed at 700 degrees Celsius to yield a final thickness of 1 μm. The PZT was patterned using standard photolithography followed by a wet etch ($10H_2O:10HCl:1HF$). The underlying Ti/Pt bottom electrode was then patterned, as shown in FIG. 5B, using argon ion milling. The platinum extends over the cantilever and mirror portions of the device because the ion milling process results in an increased surface roughness that should be avoided for the mirror. Next, a thin layer of silicon dioxide (100 nm) was deposited by PECVD to prevent shorting between the top and bottom metal layers. This layer was removed from both the mirror portion and the actuation cantilever portion using reactive ion etching (RIE).

FIG. 5C shows the top actuation electrode which was deposited by electron beam evaporation of Ti/Au/Ti (25 nm/125 nm/25 nm) (separate metal layers not shown) and patterned with a standard photoresist liftoff process. The first Ti layer improves adhesion of the gold to the underlying PZT or oxide. The top layer of Ti is provided to promote adhesion of the subsequent insulating layer to the gold electrode.

An insulator, shown in FIG. 5D, was deposited for example by PECVD in order to balance the stress in the cantilever portion of the device. Both silicon dioxide and silicon nitride layers can be used effectively for this purpose. By varying PECVD deposition parameters, a range of film stresses can be obtained. Finite element modeling was used to predict the thickness of insulator of a particular stress required to form cantilevers with minimum native curl. This thickness varied from 140 nm to 850 nm depending on the PECVD deposition parameters and the thickness of the initial thermal silicon dioxide layer. After the deposition, the top insulator was patterned using standard photolithography and etched by RIE. The base thermal oxide layer was also etched during this process.

To form the reflective mirror surface shown in FIG. 5E Ti/Au (20 nm/100 nm) was deposited and patterned in a photoresist liftoff process. Finally, as shown in FIG. 5F, in order to protect the mirror surface during the processing of the back sides of the wafers, parylene-C was vapor deposited over the entire top surface of the wafer. Parylene is a conformal polymer that is resistant to the solvents used in subsequent photolithography steps, but yet can be easily removed in an oxygen plasma.

FIGS. 6A-6D are schematics of other steps in the MEMS fabrication process of the present invention.

A two-step deep reactive ion etching (DRIE) process was used on the backsides of the wafers to remove the silicon from underneath the cantilever portion of the devices for maximum actuation capability while leaving a controlled thickness of silicon underneath the mirror portion of the devices for maximum mirror flatness. As shown in FIGS. 6A-6D, the process used a photoresist mask for the first etch and an oxide mask for the second etch.

Figure 6:
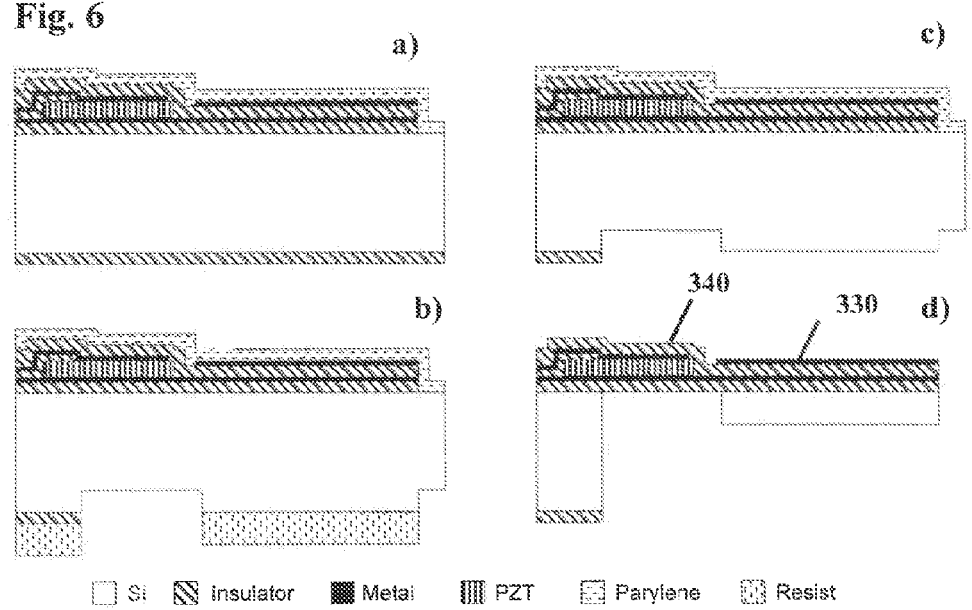
FIGS. 6A-6D are schematics of other steps in the MEMS fabrication process of the present invention.

First the oxide hard mask, shown in FIG. 6A, was patterned using standard photolithography and etched using an inductively coupled plasma etch tool (Surface Technology Systems Advanced Oxide Etch). The resist mask, as shown in FIG. 6B, was then patterned using standard photolithography to protect the area underneath the mirror during the first etch. The silicon was etched 5-30 μm by DRIE (Surface Technology Systems Advanced Silicon Etch) to give the area underneath the cantilever and surrounding the mirror a "head start." Therefore, this area will clear ahead of the area underneath the mirror in the subsequent etch.

Following this first etch, the resist mask was removed in solvent (see FIG. 6C). The wafers were then partially diced to enable the devices to be snapped apart after completion. Next, the front sides of the wafers were coated with a laminate photoresist for protection of the minor surfaces and then mounted to a silicon carrier wafer using thermally conductive epoxy. Using the previously patterned oxide mask, the remainder of the silicon was etched to clear the silicon from underneath the cantilever, as shown in FIG. 6D, and to release the devices from the surrounding substrate. Finally, the laminate photoresist and the parylene on the front sides of the mirrors were removed in an oxygen plasma.

FIGS. 7A-7D are schematics of another MEMS fabrication process of the present invention. In these figures, an alternative process using silicon-on-insulator (SOI) wafers was also demonstrated. These wafers contain a buried layer of silicon dioxide underneath the device layer silicon. In this process, the thickness of the silicon remaining underneath the mirror will be the thickness of the device layer silicon. The processing on the front sides of the wafers was identical to that which was previously described for the standard wafers. The backside process differed as shown in FIGS. 7A-7D. For the backside processing, an oxide mask and a resist mask were formed as previously described. Using the resist mask to protect the region under the minor, the silicon was etched approximately 10 μm in the area underneath the cantilever and surrounding the mirror and cantilever (see FIG. 7A). The resist mask was then removed in solvent, and the wafers were partially diced and covered in laminate photoresist to protect the mirror surfaces. The wafers were mounted to silicon carrier wafers with thermal epoxy and then etched using the previously patterned oxide mask.

As shown in FIG. 7B, this etch stopped on the buried oxide layer except in the mirror region where approximately 10 μm of silicon remained. Next, the buried oxide layer was etched using RIE. The silicon underneath the mirror served as an etch mask so that the buried oxide remained under the mirror, as shown in FIG. 7C. The wafers were then etched using another DRIE step. In this etch, the silicon was completely removed in the areas where the buried oxide was cleared and also removed from below the buried oxide in the mirror region. The end result, shown in FIG. 7D, was that the device layer silicon and the buried oxide layer remained underneath the mirror but silicon was cleared underneath the cantilever and in the surrounding regions.

Figure 8A:
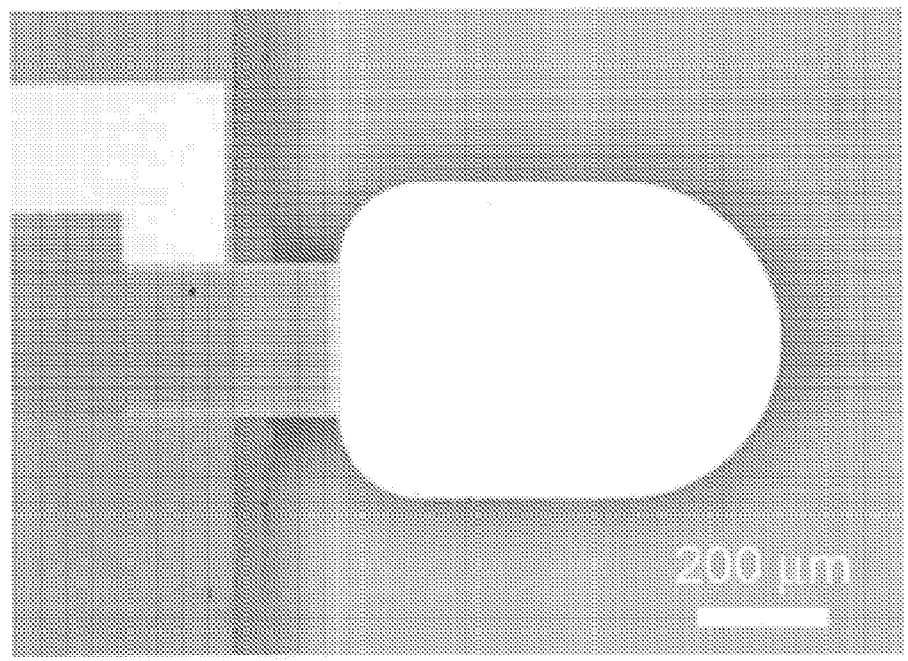
FIGS. 8a and 8b are depictions of two cantilevered mirrors produced by the MEMS fabrication process of the present invention.
Figure 8B:
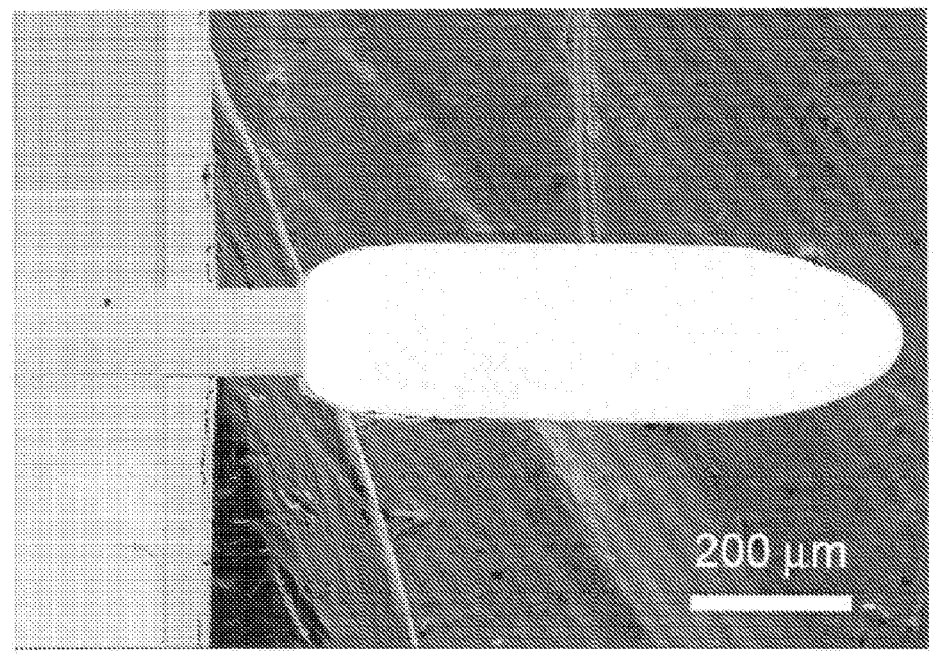

Using the above described process, devices were fabricated with mirror dimensions ranging from 500×500 μm to 840× 1600 μm. The dimensions provided here are only for illustration purposes and are not provided to limit the invention. The length of the cantilever arm ranged from 200-500 μm. The thickness of the cantilever arm ranged from 1.5 μm to 3 μm and the thickness of the mirror ranged from 8-20 μm. Optical and scanning electron micrographs of completed mirrors are shown in FIG. 8.

With reference again to FIG. 4, a detailed description of the construction of assemblies 300 will now be provided.

A single cantilever-based mirror 330 is mounted using a V-groove 310. V-grooves are commonly obtained by silicon micromachining, although also laser drilling and other mechanical machining processes can be used. Silicon micromachining of V-grooves is a batch process involving the anisotropic wet etching of single-crystal silicon wafers to expose specific crystalline surfaces. The most commonly used anisotropic etches for Si use basic solutions (KOH, for example) that preferentially etch the {100} over the {111} surfaces, and therefore produce structures resulting in exposed {111} surfaces with the characteristic sidewall angle of 54.7° in the (100) silicon wafers. Techniques to produce smooth 45° sidewalls 312, 314 have also been developed for optoelectronics applications, using KOH with isopropyl added to reveal {111} on 9.7 degree off-axis cut (100) wafers and to reveal {110} planes in (100) (JMEMS, Strandman et al, 4 (1995) 213). The groove depth (and related width) must be selected based on the thickness of the cantilever mirror handle 320 (typically 350-500 µm). The cantilever arm 340 is expected to be flat because of appropriate stress balance of the thin films. A few degrees of tilt due to residual stress can be corrected by applying an electrical DC bias to the device to achieve accurate alignment of the optical beam.

The device is bonded to the V-groove using a suitable gluing thin film, which can be deposited with a variety of mechanisms, most notably spray-coating, but also spin-coating, dip-coating, and evaporation. The V-groove may also contain patterned metal pads for electrical connection to the cantilever using wire bonds or conductive epoxy. Metal traces and pads can be obtained by evaporation, sputtering, plating, screen-printing or other methods. The V-groove base block may be used as more robust support for electrical connection to the device from the catheter wires.

Figure 9A:
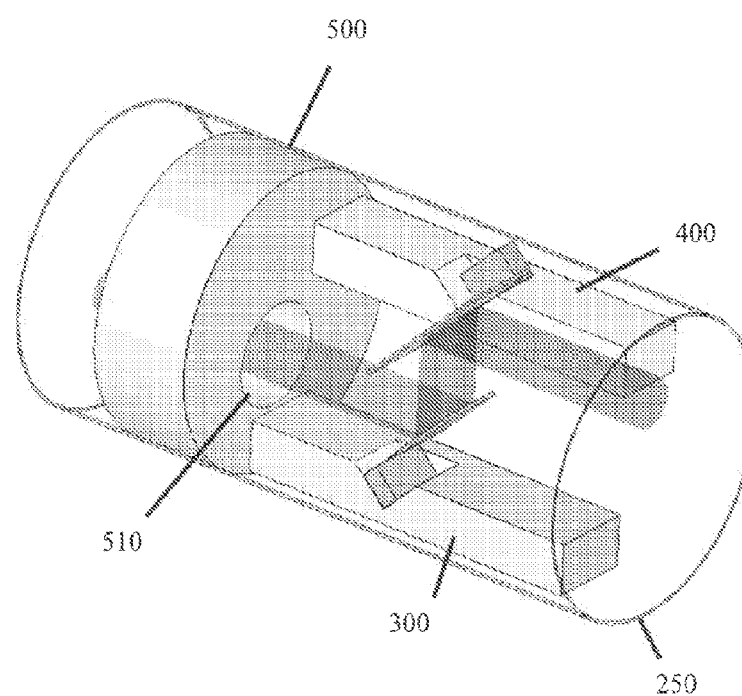
FIG. 9A is an assembly schematic of the scanning probe of the present invention.
Figure 9B:
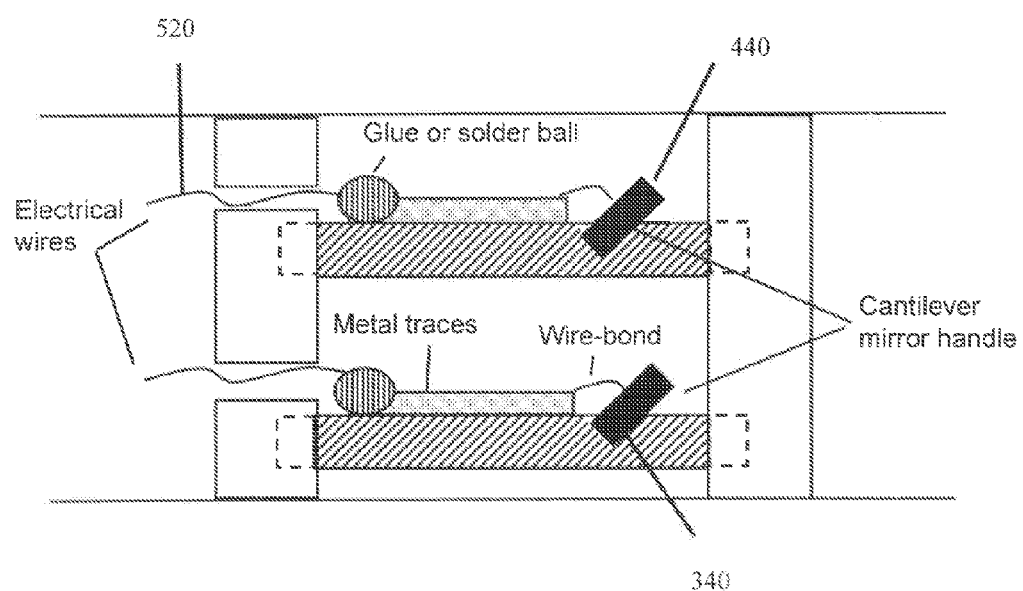
FIG. 9B is a side view of the FIG. 9 schematic illustrating the electrical connections.

FIG. 9a is an assembly schematic of the scanning probe of the present invention. As shown in FIG. 9a, two V-groove base blocks each with a cantilever-based device at the proper orientation can then be assembled together orthogonally to a cylindrical base-mount 500 contained in housing 250 (see FIG. 9a). The cylindrical base mount 500 can be designed with a cylindrical exterior to match the inner diameter of a catheter to which it is inserted. The cylindrical base mount 500 includes openings 510 for optical beam transmission of the light to and from the mirror assemblies. A thin film bonding layer can be used to attach the V-groove base blocks 350 and 450 to the cylindrical mount. The cylindrical mount can then be pressed or otherwise affixed inside the housing. FIG. 9b illustrates the electrical wiring connections 520 of the assembly of FIG. 9a.

The cylindrical mount in FIG. 9a can be obtained by milling or other the machining of materials such as metal or polymer or by silicon micromachining.

Hence, in general, there is provided a method for making an optical scanning probe which fabricates on a first base a first moveable mirror, fabricates on a second base a second moveable mirror, attaches a support to the first and second bases so that the first moveable mirror and the second moveable mirror are opposed to each other; and mounts the support in a housing having a longitudinal axis extending in a direction towards a sample to be scanned. The first moveable mirror and the second moveable mirror are disposed along the longitudinal axis apart from each other. At least one of the first and second mirrors are angularly separated from respective first and second bases at a position between a range of positive and negative angular motion for at least one of the first and second mirrors.

Besides those configurations described above, not all of the components need to be included. For example the present invention in one embodiment provides for a forward looking optical probe including a housing having a longitudinal axis extending in a direction towards a sample to be scanned, a first base having a first moveable mirror supported thereon by a cantilever connecting the first moveable minor to the first base, a second base having a second mirror, and a support attaching the first and second bases so that the first moveable mirror and the second mirror are disposed across the longitudinal axis from each other to provide forward imaging of the sample. In this arrangement, the cantilever is angularly separated from the first base at a position between a range of positive and negative angular motion for the first moveable mirror.

The present invention in one embodiment provides for an optical probe including a housing having a longitudinal axis extending in a direction towards a sample to be scanned, and a base connected to the housing and having a moveable minor supported thereon by a cantilever connecting the moveable mirror to the base. In this arrangement, the cantilever is angularly separated from the base at a position between a range of positive and negative angular motion for the minor.

Operation of the Optical Scanning Probe

In one medical application, the optical beam of FIG. 1B is delivered inside a catheter via a suitable optical fiber. For OCT probes, single mode optical fibers are typically used. In one embodiment of the invention, non-linear optical imaging is used. In this embodiment, a pulsed light source is used, and a suitable fiber-based light delivery system, such as a photonic crystal fiber, is used to preserve the properties of the pulsed light source.

A light beam, as shown in FIG. 4B which is divergent out of the fiber is collimated by a graded-index lens (GRIN) to a desired beam aperture. A typical beam size (or aperture) value for an OCT probe is 500 µm. The beam size affects the scanning mirror sizes, as the mirrors should intercept the beam in all scanned positions. A large value of beam aperture provides better resolution, but requires larger mirrors and therefore a larger diameter probe. After the beam is passed through the scanner, it must be focused on the sample. The focusing optical component to be used depends on the optical imaging techniques and can be for example an objective for confocal and multi-photon microscopy or an aspheric lens for OCT.

For OCT imaging, a suitable component is an aspheric lens with focal length (f) of 5 mm. The lens is typically positioned at a distance equal to the focal length to satisfy the telecentric condition and minimize aberration, and focuses on the sample at approximately a focal length distance. The lens can also used as whole or part of the surface that caps the catheter. The scanning range in the sample can be set to about ±1 mm. As an example, lenses with f=5 mm, diameter 2 mm, clear aperture 1.5 mm, max thickness 1 mm, min thickness 0.8 mm are commercially available; also lenses such as JML Optical, TRP14340/100, 6.5 mm diameter, f=7.9 mm can be used to accommodate this scanning range. The catheter diameter must be such that the beam is intercepted by the focusing lens at all scanned angles. Non-telecentric lens arrangements are also possible, with suitable aberration correction performed in the system.

This cascaded design in one embodiment of the invention produces a beam displacement from the center of the catheter. If constraints on the catheter dimensions require, the beam can be displaced back to the center of the catheter by a suitably designed rhomboid microprism. Rhomboid prisms translate a light beam without changing its angle. The prism can be placed between the cantilever-mirror and the focusing lens. Another possible configuration is one in which the cantilever mirrors are fabricated with a built-in curvature and act as focusing elements in addition to their function as beam scanning elements. In such case, the catheter tip can be capped with a flat transparent window.

Important figures of merit for optical scanners are the scanning angular range and the resonance frequency. In static and near static condition with a voltage range of +/−10 V, devices of the present invention with a arm thickness of 1.75 µm (of which 1 µm consisted of PZT) exhibited a mechanical angle scanning range of up to +/−3 degrees around the starting position for cantilever length of 200 µm and +/−7 degrees around the starting position for cantilever length of 400 µm. These angular displacements are mechanical angle values; therefore, optical deflection of an optical beam bouncing off the mirrors is twice as large. A voltage bias, typically less than 5V, is superimposed to the oscillating driving voltage to optimize the mechanical scanning range. The use of bipolar instead of unipolar driving voltage has the advantage of maximizing the mechanical performance of the device with the smallest possible voltage and therefore less electrical stress (i.e. potential for dielectric breakdown) on the actuator material and reduced power consumption.

The dynamic response of the system, i.e. how fast the scanner can reach the required position, depends on its resonance frequency, a property affected mainly by the cantilever stiffness and the mass of the system. For practical applications, the resonance frequency determines the largest speed at which the system can be actuated. It is well-known that arbitrary driving waveforms should be well-below the resonance frequency of the system (for example, 10 times lower). Linear waveforms and sawtooth linear waveforms such as those of FIG. 4D are possible if their frequency is well below the resonance frequency of the system. If the scanner is driven at the resonance frequency, the displacement exhibits a sinusoidal waveform of such frequency. Resonance frequencies of 1-2 kHz were measured for the optical scanners of this invention, with higher values exhibited by the shorter cantilever devices. According to known relationships for piezoelectric cantilevers, decreasing the arm thickness would increase the scanning range and decrease the resonance frequency (for example, an increase of 46% in angular displacement and a decrease of 20% in resonance frequency at 400 µm cantilever length is calculated for decreasing the PZT thickness from 1 µm to 0.8 µm). Therefore the microfabrication method of the cantilever mirror permits flexibility in the determination of the resonance frequency of specific devices.

Applications

The probes of the present invention provide novel structural and operational characteristics that permit their application in a number of different applications and permit the probe to be used in conjunction with a number of different scanning and diagnostic techniques. While the discussion below is directed primarily to medical applications, the probes can be used in non-medical applications as well where interior viewing is desirable.

For medical applications, the optical imaging systems of the present invention can be used as a forward looking 2D scanning probe operated for OCT, single-photon fluorescence, multiphoton fluorescence, laser scanning confocal fluorescence, coherence anti-Stokes Raman microscopy and other nonlinear optical imaging techniques. These imaging systems can be separated into optical engines and probes. An optical engine can include the light source(s) and detector(s) as well as the mechanisms such as interferometers, pinholes, or filters, etc that permit realization of specific imaging techniques. The probe as discussed above can include an optical fiber for light delivery to and from the sample and a scanning mechanism to raster a 1D or 2D array of sample points. Fluorescence-based imaging for tissue analysis on animal models or humans utilizes injected and natural fluorescent markers, which would then be excited by the light source and the fluorescence collected through the probe of the present invention. A dichroic minor is typically used along the beam path to separate excitation and emission wavelengths.

The probe of the present invention can be used in scanning confocal microscopy where a laser beam focused to a spot on the sample to excite fluorescence, and a spatial pinhole is used to remove the out-of-focus fluorescence from the region outside the focus spot. This technique enables submicron lateral resolution fluorescence imaging with depth information ranging from 0 to 250 µm. A 2D image is created by scanning the focused spot in the sample. Depth information can be obtained by changing the longitudinal position of the focusing lens with mechanical movement by mechanisms which are outside the scope of the present invention. Endoscopic light delivery to the sample can be achieved by the use of suitable single mode optical fibers to deliver illumination and capture fluorescent signal as well as acting as pinholes. The light beam goes to and from the sample through the scanning apparatus of this invention as shown in FIG. 4.

Single-photon fluorescence images are often produced with a continuous source while multiphoton imaging removes out-of-focus fluorescence by using two or more photons from a long-wavelength, near-infrared pulsed laser which excites fluorescent probes in only a single optical section and without phototoxic side-effects. (See Denk et al., "Two-Photon Laser Scanning Fluorescence Microscopy," Science, vol. 248, Apr. 6, 1990, pp. 73-76, the entire contents of which are incorporated herein by reference). Multi-photon fluorescence microscopy is capable of high lateral resolution (<1 µm) and larger depths than confocal microscopy (several hundred µm, according to Jung and Schnitzer, Optics Letters 28, 902 (2003), the entire contents of which are incorporated herein by reference) because the non-linear and more rapid decay of fluorescent signal from the focal plane reduces out-of-plane scattering and because it avoids the use of lossy pinholes used in confocal microscopy.

The implementation of endoscopic multi-photon fluorescent microscopy is complicated by the fact that conventional single mode fibers degrade the pulsed laser optical signal-which can be addressed using either hollow core, fiber bundles or double cladding photonic crystal fibers.

The probe(s) of the present invention can be used in conjunction with other non-linear optical imaging techniques, such as second harmonic generation endoscopy and Coherent anti-Stokes Raman scattering (CARS) endoscopy, which are sensitive to structural rather than chemical features of the sample. These techniques obtain contrast without the need for fluorescent labeling. Second harmonic generation tomography relies on femtosecond laser sources, and is sensitive to anisotropic structures because the signal depends on the orientation and polarization of chiral molecules, such as collagen fibrils, myofilaments, and polarized microtubule bundles. See Guo et al., "Second-harmonic tomography of tissues," Opt. Lett., 22(17):1323-5, (Mar. 3, 1997), the entire contents of which are incorporated herein by reference.

Coherent anti-stokes Raman scattering (CARS) imaging provides for the analysis of chemical and biological samples by using molecular vibrations as a contrast mechanism. See Xie, et al. U.S. Pat. No. 7,414,729, the entire contents of which are incorporated herein by reference. CARS requires the use of at least two pulsed laser beams (a pump source and a Stokes source) with slightly shifted frequency creating a coherent anti-Stokes field in the sample; when the frequency difference is tuned to be resonant with a given vibrational mode, an enhanced signal is observed at the anti-Stokes frequency. This method permits the use of lower average excitation powers and/or shorter data collection times than other techniques using pulsed laser illumination.

Scanning units of the present invention can be interfaced with optical fiber techniques and coupled to catheters, endoscopes, laparoscopes, biopsy needles and surgical probes. An endoscope, such as for example used for a colonoscopy, has an outer diameter ranging from 9 to 12 mm, contains a working channel and may contain an accessory channel which allows the insertion of a removable catheter (typically 2.8 mm to 4 mm in diameter). A catheter diameter in medicine typically ranges from 1 mm to 11.3 mm. The OCT capable scanning units of the present invention are of a suitably small size that these units can be inserted inside the endoscopic probe and removed to enable the addition of OCT imaging or other image modality as described above. Accordingly, other catheter-based devices can be inserted into and removed from this channel, which avoids the rather complex procedure of removing and re-inserting the entire endoscope into the patient.

The scanning unit of the present invention can be interfaced with optical fibers and used in conjunction with optical imaging modalities for non-medical endoscopic imaging, for example for inspection and non destructive evaluation of systems and materials, such as the inside of engines or structural components of buildings or inside pipes and other conduits carrying electrical wires or fluids.

The scanning unit of the present invention can be interfaced with optical fibers and catheters and used in a non-imaging application, to provide a light beam scanning through small openings for laser therapy, including laser-induced wound healing, tissue ablation, and coagulation.

Numerous modifications and variations of the invention are possible in light of the above teachings. It is therefore to be understood that within the scope of the appended claims, the invention may be practiced otherwise than as specifically described herein.

The invention claimed is:

1. A medical optical scanning apparatus comprising:
   a housing having a longitudinal axis extending in a direction towards a sample to be scanned;
   a first base having a first moveable mirror supported thereon by a first cantilever connecting the first moveable mirror to the first base;
   a second base having a second moveable mirror supported thereon by a second cantilever connecting the second moveable mirror to the second base;
   a support attaching the first and second bases so that the first moveable mirror and the second moveable mirror are disposed along the longitudinal axis apart from each other to provide scanning in two complementary directions; and
   one of the first and second cantilevers angularly separated from a respective one of the first and second bases at a position between a range of positive and negative angular motion for at least one of the first and second mirrors.

2. The apparatus of claim 1, wherein at least one of the first moveable mirror and the second moveable mirror comprises a cantilevered mirror.

3. The apparatus of claim 2, wherein at least one of the first moveable mirror and the second moveable mirror comprises a piezoelectric driven cantilever.

4. The apparatus of claim 1, wherein:
   the first moveable mirror is configured to deflect in a first angular direction,
   the second moveable mirror is configured to deflect in a second angular direction, and
   the first angular direction and the second angular direction deflect in mutually different planes.

5. The apparatus of claim 4, wherein the first moveable mirror has a range of angular movement centered at an angle of 45° from the longitudinal axis.

6. The apparatus of claim 5, wherein the range of angular movement is no less than 5° and no more than 85°.

7. The apparatus of claim 4, where the second moveable mirror has a range of angular movement centered at an angle of 45° from the longitudinal axis.

8. The apparatus of claim 7, wherein the range of angular movement is no less than 5° and no more than 85°.

9. The apparatus of claim 4, wherein:
   the first moveable mirror is configured to sweep back and forth across an entire range of the first angular direction, and
   the second moveable mirror is configured to stepwise increment in the second angular direction.

10. The apparatus of claim 4, wherein at least one of the first and second moveable mirrors is configured to sweep back and forth at frequencies ranging from 0 to 10 kHz.

11. The apparatus of claim 4, wherein at least one of the first and second moveable mirrors is configured to sweep back and forth using a triangular or sawtooth or other linear waveform.

12. The apparatus of claim 4, wherein at least one of the first and second moveable mirrors is configured to sweep back and forth using a sinusoidal waveform at any frequency up to the resonance frequency of the system.

13. The apparatus of claim 1, wherein at least one of the first and second moveable mirrors has a mirror area larger than 100 $\mu m^2$ and smaller than 25 $mm^2$.

14. The apparatus of claim 1, wherein at least one of the first and second moveable mirrors comprises a larger mirror in area than the other of the first and second moveable mirrors.

15. The apparatus of claim 1 wherein at least one of the first and second moveable mirrors comprises a rectangular mirror with an aspect ratio of length/width greater than 1, and the other of the first and second moveable mirrors comprises a rectangular mirror with an aspect ratio of length/width less than 1.

16. The apparatus of claim 1, wherein the housing comprises a cylindrical housing having an outside diameter sized to insert in a medical catheter.

17. The apparatus of claim 1, further comprising:
   a collimating lens configured to collimate light from an optical source and direct the light to the first moveable mirror;
   and a focusing lens configured to focus light from the second moveable mirror to the sample,
   wherein the collimating lens and the focusing lens comprise a part of an optical probe.

18. The apparatus of claim 17, wherein the optical probe comprises a forward-looking probe.

19. The apparatus of claim 17, wherein the optical probe comprises a probe inserted in a medical catheter.

20. The apparatus of claim 19, wherein the probe inserted in the medical catheter has an outer diameter ranging from 1 mm to 11.3 mm.

21. The apparatus of claim 17, further comprising an optical fiber for optical communication to and from the optical probe.

22. The apparatus of claim 1, wherein:
   the housing comprises a cylindrical housing; and
   the support comprises a cylindrical support.

23. The apparatus of claim 1, further comprising electrical leads for delivery of a driving voltage to the first and second movable mirrors.

24. A medical optical scanning system comprising:
an optical scanning probe configured to image a sample at different lateral positions of the sample, and comprising,
a housing having a longitudinal axis extending in a direction towards a sample to be scanned,
a first base having a first moveable mirror supported thereon by a first cantilever connecting the first moveable mirror to the first base,
a second base having a second moveable mirror supported thereon by a second cantilever connecting the second moveable mirror to the second base,
a support attaching the first and second bases so that the first moveable mirror and the second moveable mirror are disposed along the longitudinal axis apart from each other to provide scanning in two complementary directions, and
one of the first and second cantilevers angularly separated from a respective one of the first and second bases at a position between a range of positive and negative angular motion for at least one of the first and second mirrors; and
an optical engine connected to an optical scanning probe.

25. The system of claim 24, wherein at least one of the first moveable mirror and the second moveable mirror comprises a cantilevered mirror.

26. The system of claim 24, wherein at least one of the first moveable mirror and the second moveable mirror comprises a piezoelectric driven cantilever.

27. The system of claim 24, wherein:
the first moveable mirror is configured to deflect in a first angular direction,
the second moveable mirror is configured to deflect in a second angular direction, and
the first angular direction and the second angular direction deflect in mutually different planes.

28. The system of claim 27, wherein:
the first moveable mirror is configured to sweep back and forth across an entire range of the first angular direction, and
the second moveable mirror is configured to stepwise increment in the second angular direction.

29. The system of claim 24, further comprising:
a light source for illumination of a sample to be scanned; and
a detector configured to collect light reflected or emitted from the sample.

30. The system of claim 29, wherein:
the light source comprises a non-coherent light source;
said non-coherent light is rastered by the first and second moveable mirrors, and
the detector detects the light reflected from the sample.

31. The system of claim 30, further comprising:
a processor configured to perform Fourier domain processing on the detected non-coherent light reflected from the surface of the sample to image the surface of the sample.

32. The system of claim 31, wherein the processor is configured to perform optical coherence tomography.

33. The system of claim 29, wherein:
the light source comprises a coherent light source,
said coherent light is imaged on the surface of the sample, and
the detector detects fluorescent light reflected from the sample.

34. The system of claim 33, further comprising:
a processor configured to perform chemical mapping based on the detected fluorescent light reflected from the surface of the sample.

35. The system of claim 24, wherein the optical engine comprises at least one of an optical coherence tomography system, a single-photon fluorescence system, a multiphoton fluorescence system, a laser scanning confocal fluorescence system, a coherence anti-Stokes Raman scattering system, and a second harmonic generation system.

36. The system of claim 24, wherein the optical engine is configured to provide a non-imaging optical modality for light-based therapy.

37. A method for making a medical optical scanning probe, comprising:
fabricating on a first base a first moveable mirror;
fabricating on a second base a second moveable mirror;
attaching a support to the first and second bases so that the first moveable mirror and the second moveable mirror are opposed to each other; and
mounting the support in a housing having a longitudinal axis extending in a direction towards a sample to be scanned such that the first moveable mirror and the second moveable mirror are disposed along the longitudinal axis apart from each other and at least one of the first and second mirrors being angularly separated from respective first and second bases at a position between a range of positive and negative angular motion for at least one of the first and second mirrors.

38. The method of claim 37, wherein fabricating on a first base a first moveable mirror or fabricating on a second base a second moveable mirror comprises: anistropically etching a groove in a semiconductor substrate; and
attaching at least one of the first and second moveable mirrors into the groove.

39. The method of claim 37, further comprising:
fabricating at least one of the first and second moveable mirrors as a cantilevered piezoelectrically-driven mirror assembly.

40. The method of claim 39, wherein fabricating at least one of the first and second moveable mirrors comprises:
depositing a bottom electrode on a sacrificial substrate;
depositing a piezoelectric layer on the bottom electrode;
depositing a top electrode on the piezoelectric layer;
patterning the top electrode and the piezoelectric layer and the bottom electrode to produce a cantilevered arm;
depositing an insulating layer over exposed edges of the bottom electrode;
depositing a stress control layer on the cantilevered arm;
depositing a reflective layer to form a mirror surface at the distal end of the cantilevered mirror assembly; and
removing a part of the sacrificial substrate to release the cantilevered mirror assembly including the reflective layer, the stress control layer, the bottom electrode, the piezoelectric layer, and the top electrode.

41. The method of claim 40, further comprising:
retaining a portion of the sacrificial substrate under at least one of the first and second moveable mirrors.

42. The method of claim 39, wherein fabricating at least one of the first and second moveable mirrors comprises:
depositing a bottom electrode on a sacrificial silicon-on-insulator substrate;
depositing a piezoelectric layer on the bottom electrode;
depositing a top electrode on the piezoelectric layer;
patterning the top electrode and the piezoelectric layer and the bottom electrode to produce a cantilevered arm;

depositing an insulating layer over exposed edges of the bottom electrode;

depositing a stress control layer on the cantilevered arm;

depositing a reflective layer to form a mirror surface at the distal end of the cantilevered mirror assembly; and removing a part of the sacrificial silicon-on-insulator substrate to release the cantilevered mirror assembly including the reflective layer, the stress control layer, the bottom electrode, the piezoelectric layer, and the top electrode.

43. The method of claim 42, further comprising:

retaining the top silicon layer of the silicon-on-insulator wafer under at least one of the first and second moveable mirrors.

44. The method of claim 37, wherein fabricating on a first base a first moveable mirror or fabricating on a second base a second moveable mirror comprises at least one or more of:

laser machining the first base or the second base;

micro-milling the first base or the second base; and silicon micromachining the first base or the second base.

* * * * *